(12) United States Patent
Mendez-Coll

(10) Patent No.: US 8,540,646 B2
(45) Date of Patent: Sep. 24, 2013

(54) BIOPSY AND SUTURELESS DEVICE

(76) Inventor: Jose Arturo Mendez-Coll, San Juan, PR (US)

(*) Notice: Subject to any disclaimer, the term of this patent is extended or adjusted under 35 U.S.C. 154(b) by 0 days.

(21) Appl. No.: 13/089,056

(22) Filed: Apr. 18, 2011

(65) Prior Publication Data
US 2012/0265096 A1   Oct. 18, 2012

(51) Int. Cl.
*A61B 10/00* (2006.01)

(52) U.S. Cl.
USPC ........... 600/568; 600/562; 600/567; 606/170; 606/219

(58) Field of Classification Search
USPC ......... 600/562–571; 606/167–180, 184–185, 606/213, 215–221
See application file for complete search history.

(56) References Cited

U.S. PATENT DOCUMENTS

| | | | | |
|---|---|---|---|---|
| 4,461,305 A | * | 7/1984 | Cibley | 600/567 |
| 4,785,826 A | * | 11/1988 | Ward | 600/567 |
| 4,951,690 A | * | 8/1990 | Baker | 128/898 |
| 5,312,023 A | * | 5/1994 | Green et al. | 227/175.1 |
| 5,357,974 A | * | 10/1994 | Baldridge | 600/567 |
| 5,725,554 A | * | 3/1998 | Simon et al. | 606/219 |
| 2002/0065535 A1 | * | 5/2002 | Kneifel et al. | 606/219 |
| 2004/0167430 A1 | * | 8/2004 | Roshdieh et al. | 600/567 |
| 2004/0249391 A1 | * | 12/2004 | Cummins | 606/139 |
| 2007/0232954 A1 | * | 10/2007 | Harris et al. | 600/564 |
| 2007/0249960 A1 | * | 10/2007 | Williamson | 600/564 |

* cited by examiner

*Primary Examiner* — Rene Towa
(74) *Attorney, Agent, or Firm* — Eugenio J. Torres-Oyola; Rafael Rodriguez-Muriel

(57) ABSTRACT

A dermal punch device for automatically extracting a sample of tissue of a predetermined size and shape from a body comprising a retractable cutter and a sutureless biopsy closure mechanism that includes a wound closure fastener member adapted to be disposed over a biopsy region after the performance of the biopsy, wherein wound closure fastener member is applied without the need of several instruments to seal the wound. The wound closure fastener member is dispensed by a sutureless biopsy closure dispenser located at the same distal end of the biopsy punch device surrounding the biopsy punch cutter assembly avoiding the need of separates instruments, reducing the wound closing steps and surgical procedure time.

12 Claims, 20 Drawing Sheets

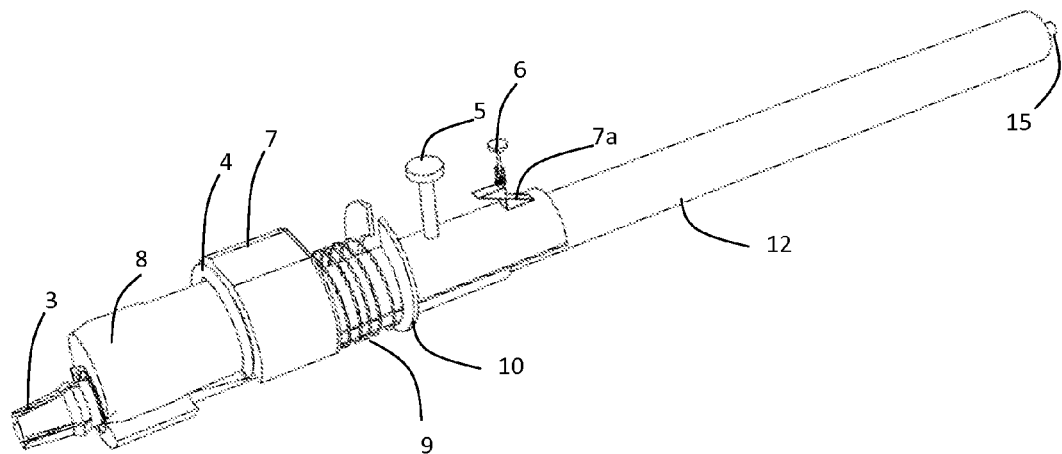
FIG. 5A
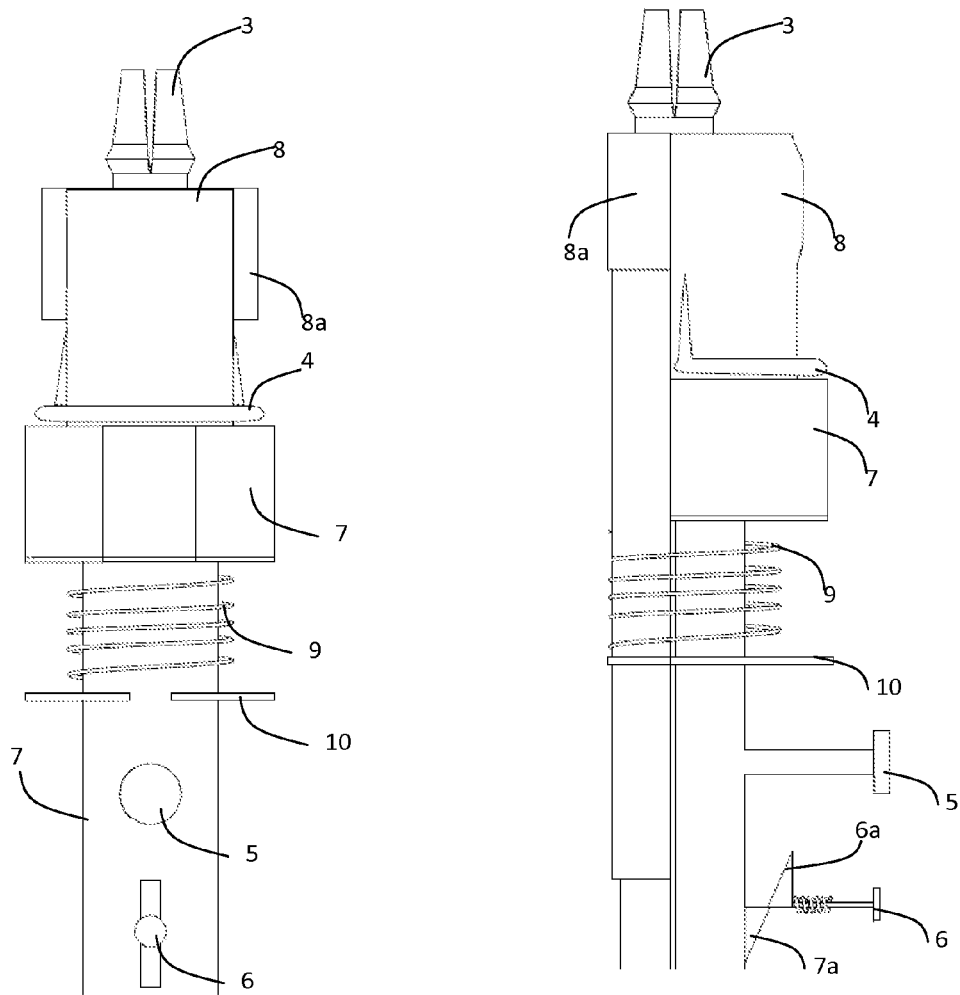
FIG. 5B
FIG. 5C

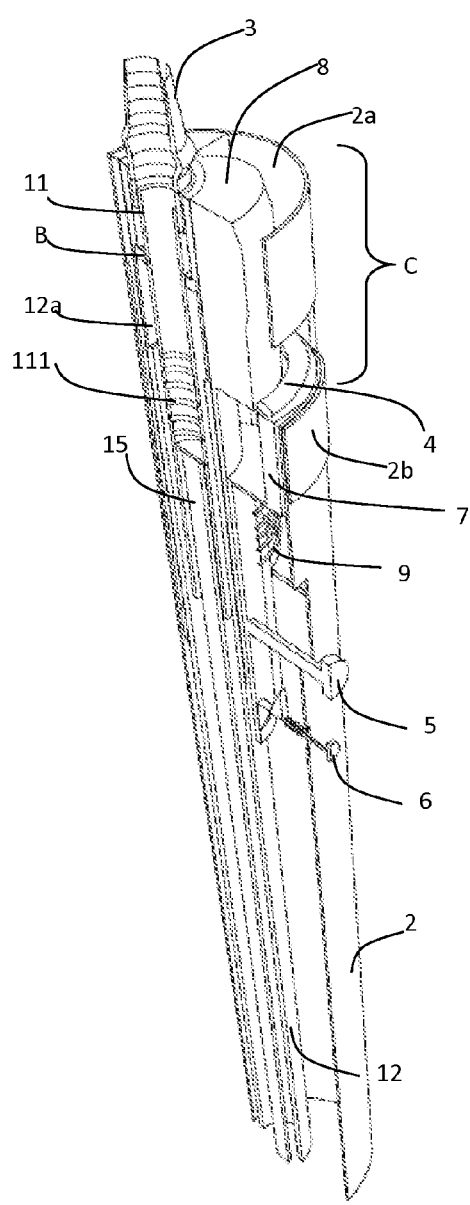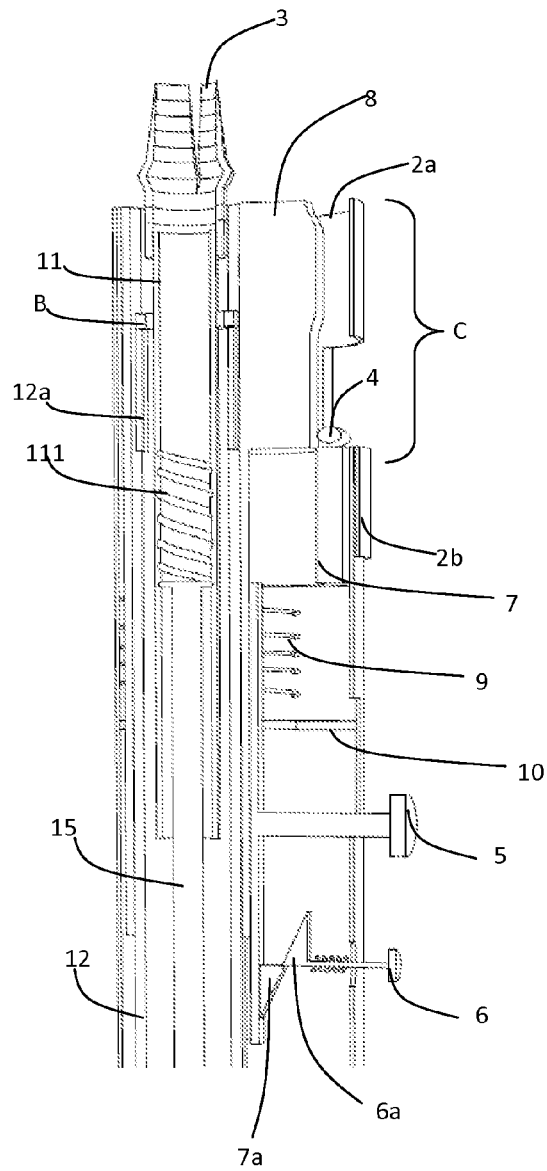
FIG. 6A
FIG. 6B

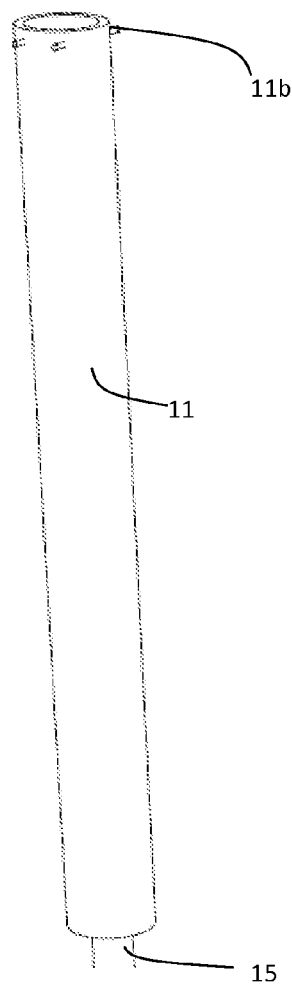
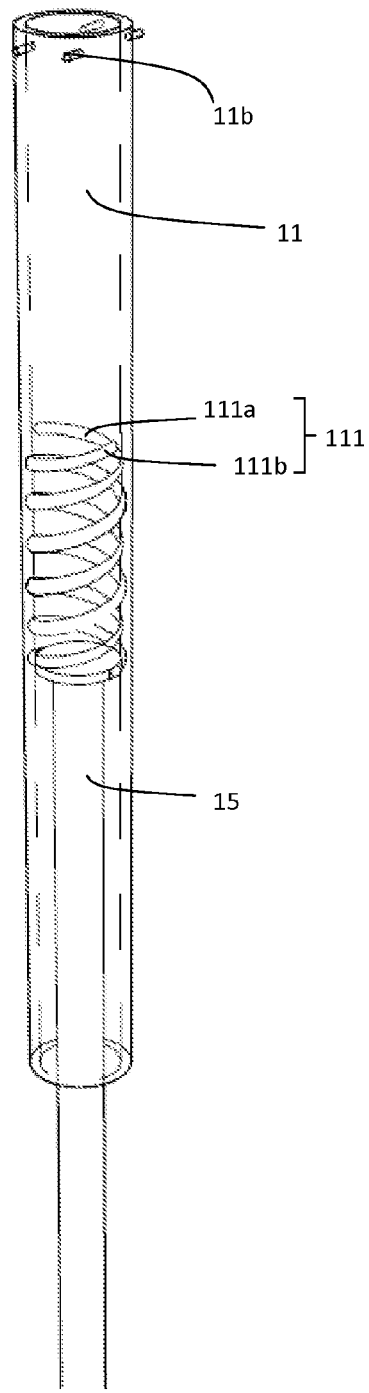
FIG. 8A
FIG. 8B

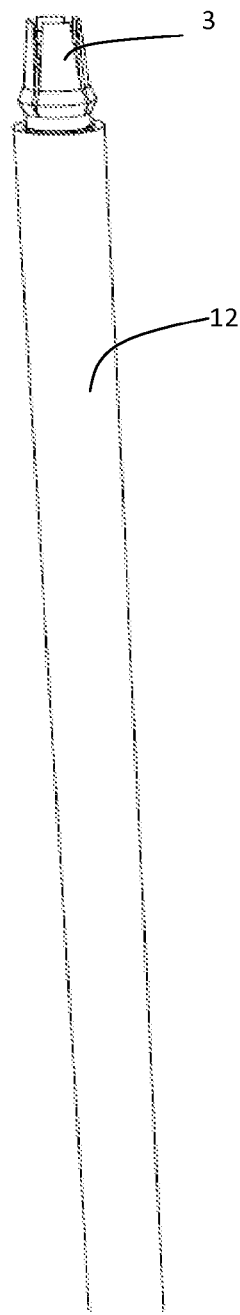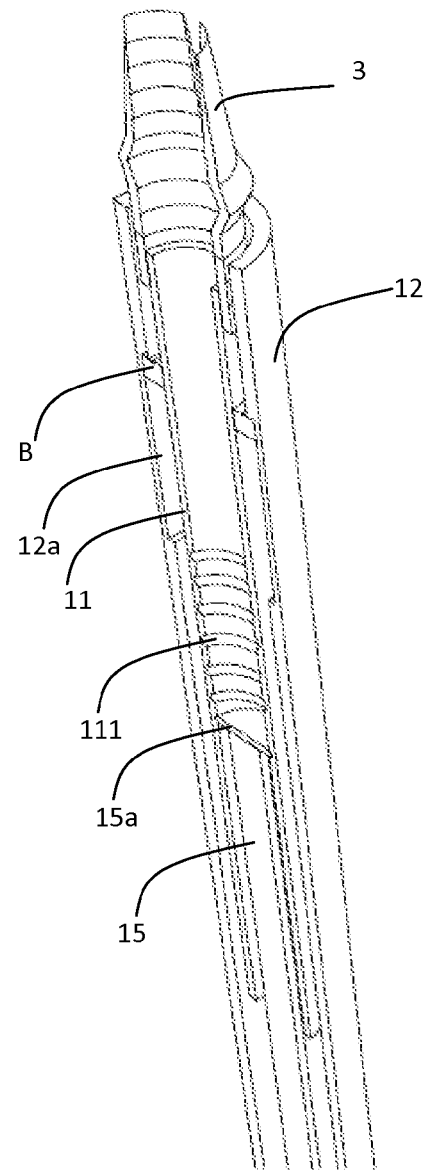
FIG. 15A
FIG. 15B

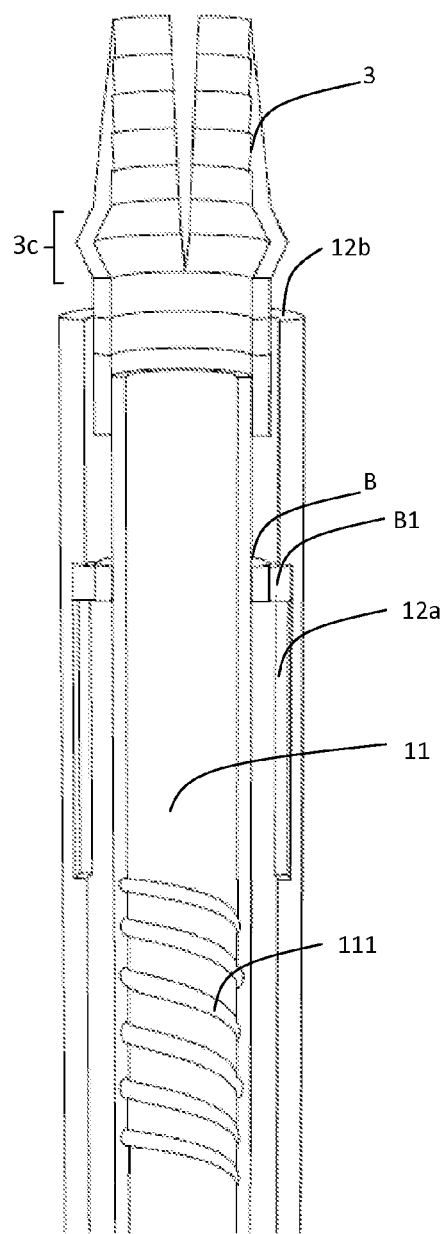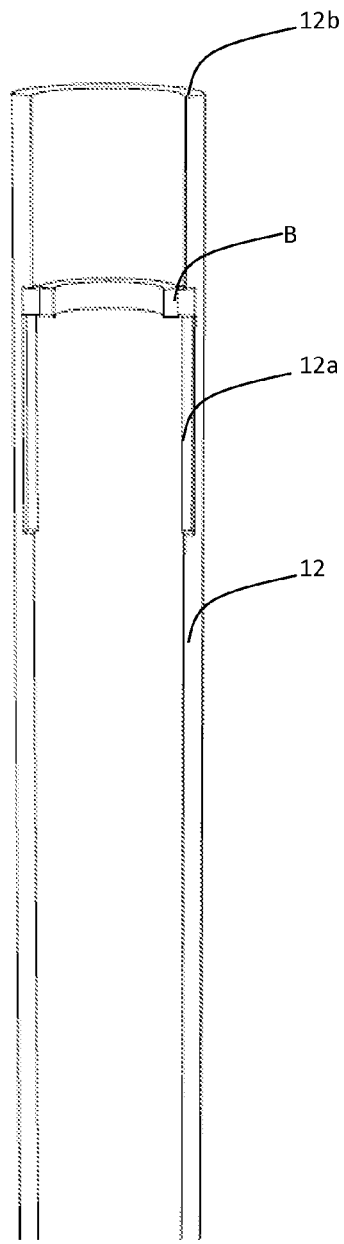
FIG. 15C
FIG. 16

BIOPSY AND SUTURELESS DEVICE

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

This application relates generally to the field of extracting tissue samples from solid bodies, and more specifically to surgical instruments for extracting a biopsy or sample of tissue while providing a sutureless biopsy wound site closure.

2. Discussion of the Background

Annually thousands of persons and animals are tested for numerous skin problems such as abnormal skin growths and cancers, as well as skin eruptions. Surgical instruments, such as a dermal punch and others are used to obtain samples of skin lesions for diagnostic purposes. The procedure involves the insertion of a cutting surgical instrument into the patient's skin wherein the cutting surgical instrument comprises a cylindrical blade at the distal end of an inert plastic or metal rod. After abutting the cylindrical blade to the skin the cutting instrument is rotated so as to cut out and remove a plug of the tissue of interest. The tissue is then submitted to be analyzed by a pathologist in order to obtain a diagnosis.

For example in a skin punch biopsy, the skin surrounding the lesion is pulled taut, and the punch is firmly introduced into the lesion and rotated to obtain the tissue specimen. The punch must go deep enough to include an average of a 6 mm depth in order to include the lower dermis and subcutaneous fat. The plug is lifted with forceps or a needle. The specimen is placed in a properly labeled sterile container.

After the removal of the tissue, the traditional dermal punch biopsy usually leaves a circular wound opening which is then normally closed by a suture. Some of the problems associated with this technique include, but are not limited to, the use of multiple instruments in performing the suturing which typically requires at least a needle holder, scissors, suture material and forceps. Other problems are the potential for a needle stick injury and the increased cost of the suture and sterilization of the instruments used. Furthermore, there is also a need for more than one person to perform the procedure, for example a nurse has to prepare a sterile instrument tray, pass the instruments to the surgeon, place a bandage on the wound following the procedure and finally pick up and resterilize the instruments.

There is a need for a device that provides a streamlined procedure which does away with the time consuming pre and post operative phase, reduces the currently needed personnel, and instruments and provides an improved sutureless wound closure at the site of the biopsy wound. It should be relatively inexpensive, easy to apply, efficient and not require subsequent procedures.

SUMMARY OF THE INVENTION

The present disclosure describes a biopsy punch device operated by a single operator, wherein the biopsy punch device comprises a mean to obtain the tissue sample while achieving sutureless closing of the biopsy wound site without a need of other instruments. The biopsy punch device cuts and extracts the tissue without lifting the device from the skin. After the tissue is removed the biopsy punch device achieves sutureless closing of the biopsy wound site without the need for additional instruments such as needles, suture material, forceps and scissors. The suture process is achieved by deploying a fastener member having resilient properties configured for this purpose.

The first embodiment of the biopsy punch device comprises an elongated hollow cylinder with a distal end having an exposed cylindrical cutter which rotates during the incision procedure and is then retracted into the body of the elongated hollow cylinder while the cylindrical cutter assists with the grasping and removing of the tissue sample and; wherein said cylindrical cutter is coupled to a sutureless fastening mechanism. The sutureless fastening mechanism comprises a sutureless dispenser to dispense a biopsy closure fastener member. The sutureless biopsy closure dispenser releases the biopsy closure fastener member at the wound site which renders the biopsy wound site closed by approximating the opposing edges of the wound. The biopsy closure fastener member comprises a two-pronged fastener having resilient properties, wherein the two-pronged fastener may expand to a distance at least equal to the diameter of the wound created by the cylindrical cutter and then contracts when released therein. The present biopsy punch device eliminates the need for multiple instruments and their handling, sutures and speeds-up the process.

It is another objective to provide a retractable biopsy punch actuated by an electric motor, wherein the biopsy punch cutter comprises a constant and uniform depth to provide a tissue specimen having a uniform thickness for accurate diagnosis.

It is a further objective to provide a biopsy punch cutter blade that is inexpensive to manufacture such that it can be made disposable.

It is a further objective to provide a biopsy punch cutter blade that is configured to assist with the removal of the tissue sample.

Another objective is to provide a method for suturing during the procedure without the need of several instruments.

Another objective is to minimize time and effort during the process of closing the wound site.

The preferred embodiment for a biopsy and sutureless device constructed pursuant to this application, both as to its configuration and its mode of operation will be best understood, and additional objects and advantages thereof will become apparent, by the following detailed description taken in conjunction with the accompanying drawings.

The applicant hereby asserts, that the disclosure of the present application may include more than one invention, and, in the event that there is more than one invention, that these inventions may be patentable and non-obvious one with respect to the other.

Furthermore, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the disclosure of the application, which is measured by the claims, nor is it intended to be limiting as to the scope of the disclosure in any way.

BRIEF DESCRIPTION OF THE DRAWINGS

The accompanying drawings which are incorporated herein constitute part of the specifications and illustrate the preferred embodiment of a biopsy and sutureless device constructed pursuant to an example embodiment of the present invention.

FIGS. 5A through 5C are several views of an exemplary biopsy punch device inner structure in accordance with the principles of the present example embodiment of the present invention.

FIGS. 6A through 6B are cross-sectional views of an exemplary biopsy punch device inner structure in accordance with the principles of the present example embodiment of the present invention.

FIGS. 8A through 8B are perspective and exploded views of an exemplary biopsy cutter shaft and motor shaft assembly in accordance with the principles of the present example embodiment of the present invention.

FIGS. 15A through 15C are perspective and exploded views of an exemplary bearing shaft, cutter shaft and cutter assembly in accordance with the principles of the present example embodiment of the present invention.

FIG. 16 is a view of an exemplary bearing shaft in accordance with the principles of the present invention.

DESCRIPTION OF THE PREFERRED EMBODIMENT

Figure 1A:
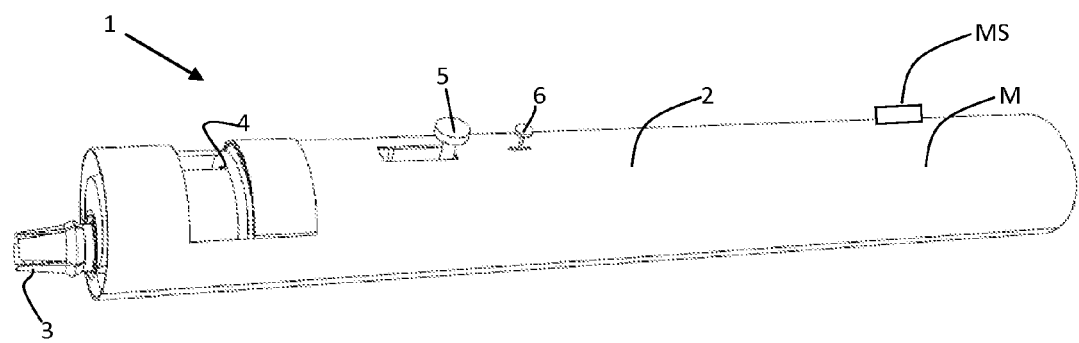
FIGS. 1A through 1B are perspective views of an exemplary biopsy punch device in accordance with the principles of the present example embodiment of the present invention.

FIG. 1A shows an exemplary biopsy punch device in accordance with the principles of the present application. The first embodiment for a biopsy punch device 1 constructed in accordance with this application comprises an elongated hollow body housing 2 with a distal end having an exposed cylindrical cutter 3, a sutureless fastener member 4, loading shaft 5, a trigger 6 and a automatic system comprising a motor M and a control system MS.

Figure 1B:
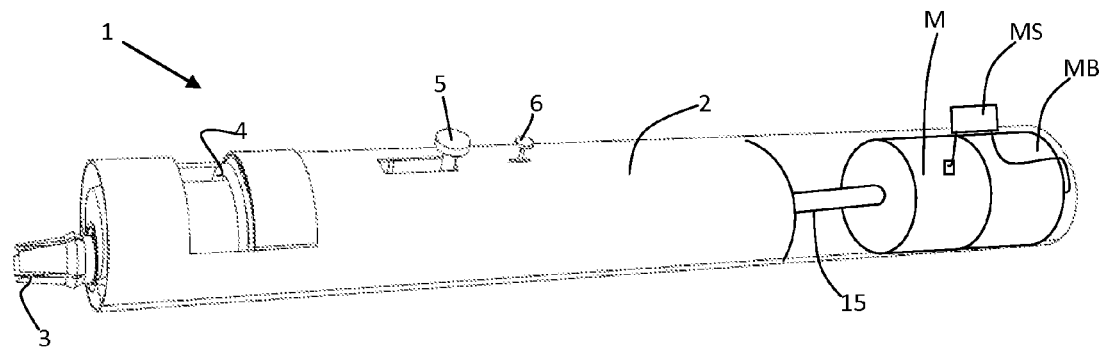

The automation system is mechanically coupled to the biopsy punch cutter 3 assembly, wherein the automation system is located at the proximal end of the elongated hollow body 2. The automation system comprises a power supply or battery MB electrically coupled to the motor M by means of a rotation control system MS, wherein the rotation control system MS regulates the behavior of the motor M, more particularly the rotation of the motor shaft 15, as shown in FIG. 1B, which is mechanically coupled to the biopsy punch cutter 3 assembly.

Figure 2:
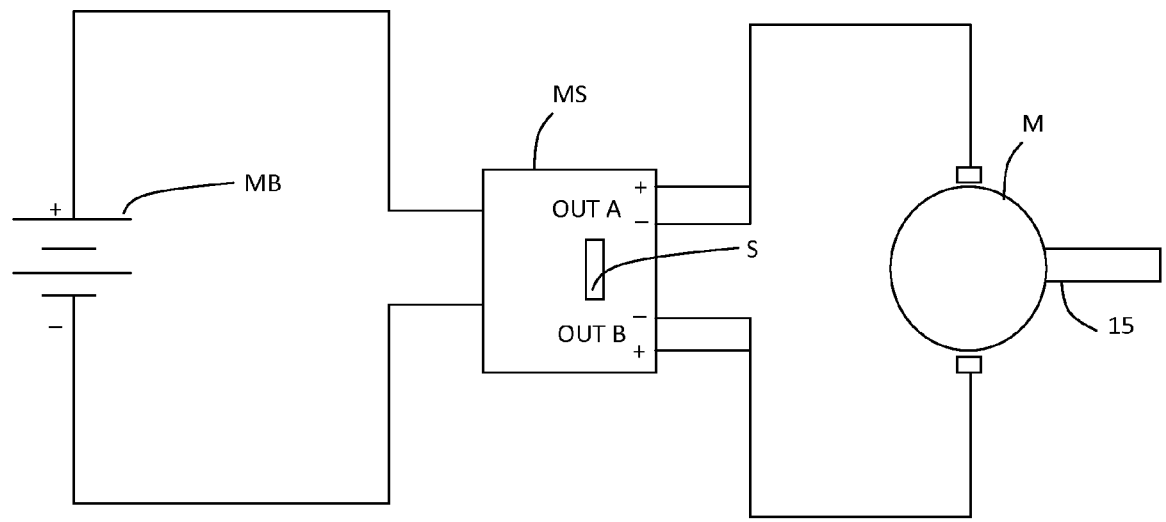
FIG. 2 is a circuit diagram of the battery, rotation control system and motor.
Figure 3A:
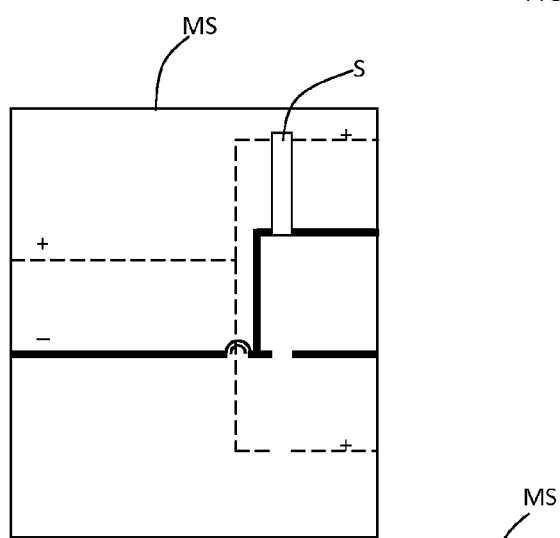
FIGS. 3A through 3C are views of the three principle stages for the rotation control system in accordance with the principles of the present example embodiment of the present invention.
Figure 3B:
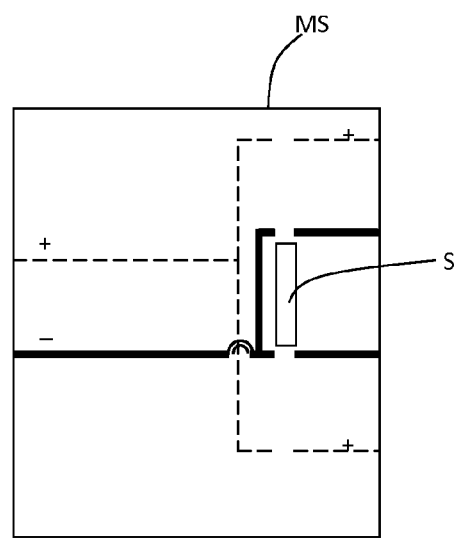
Figure 3C:
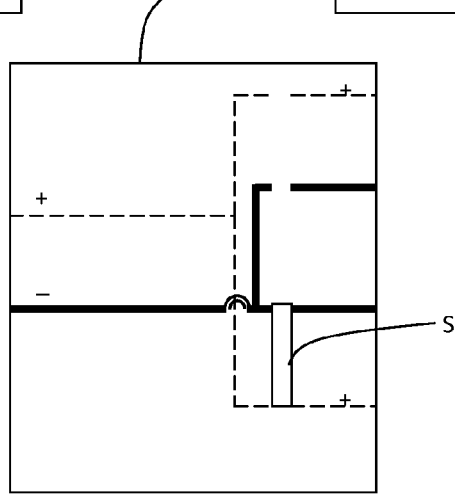

FIG. 2 represents the circuit diagram for the automation system wherein the power supply MB, such as a battery is electrically coupled to the rotation control system MS and said control system MS comprises at least two outputs connected to the motor M for controlling the shaft 15 rotation. The rotation control system MS provides at least three different stages. The three different stages are achieved, for example, using a double pole center-off, such as a Center-Off Rocker switch. The switch S diverts or regulates the current flowing to the motor, in the three different stages as mentioned. The position of the switch S with respect to the internal connection of the rotation control system MS inner circuit, as shown in FIG. 3A through FIG. 3C, provide a first stage wherein the current supplied to the motor generates a clock-wise rotation at the rotor of the motor M, as shown in FIG. 3A. FIG. 3B shows the second stage wherein no current is supplied to the motor resulting in no rotation at the rotor of the motor M and FIG. 3C shows the third stage wherein the current supplied to the motor M generates a counter clockwise rotation or a rotation direction opposed to the first stage rotation at the rotor of the motor M. Several rotation control systems MS or circuit configurations can be used to control the rotational movement of the motor M, which consequently rotates the cutter 3. However, since both pieces are mechanically coupled it is important to understand that the selection of the motor M, more particularly the rotation direction, speed and torque depends on the application of function being curried out weathers incision, pick up of tissue or retraction of the cutter 3 into the body of the elongated hollow cylinder.

Figure 4A:
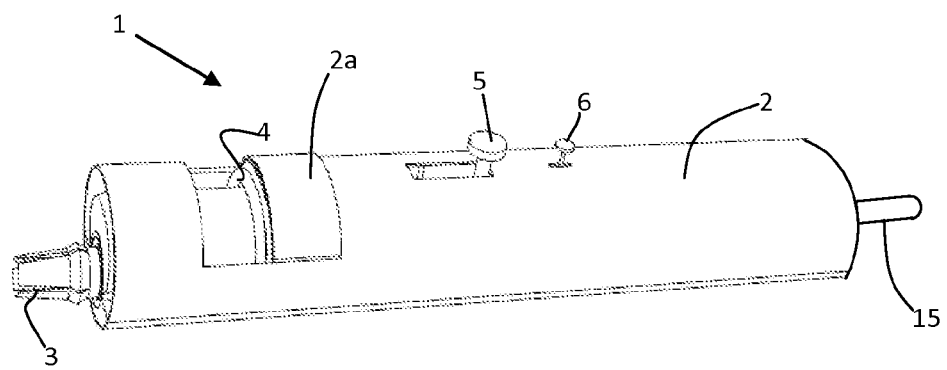
FIGS. 4A through 4B are several views of an exemplary biopsy punch device without motor and battery connection in accordance with the principles of the present example embodiment of the present invention.
Figure 4B:
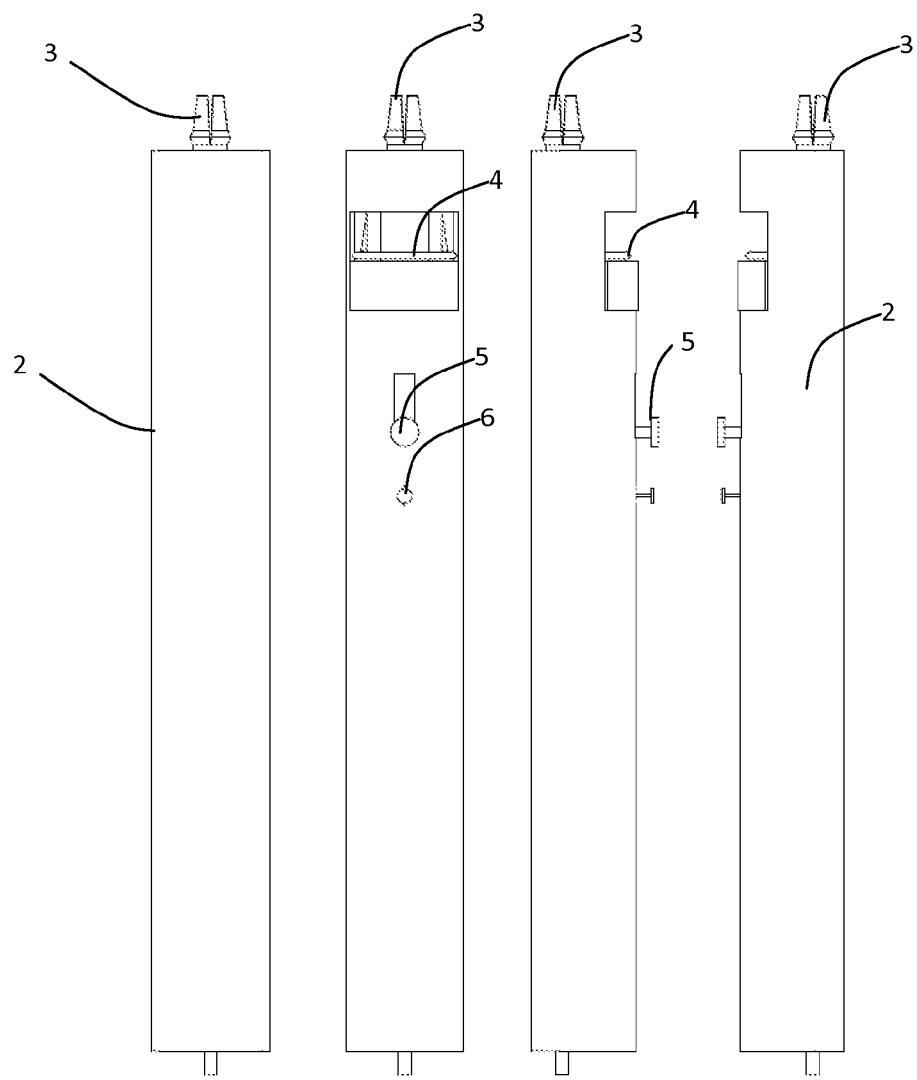

FIGS. 4A through 4B are several views of an exemplary biopsy punch device without motor and battery connection in accordance with the principles of the present example embodiment of the present invention, wherein the motor shaft 15 is mechanically coupled to the biopsy punch cutter 3 assembly. An opening is provided at the elongated hollow body housing 2. The opening serves as an entrance to a chamber C created at the front part of the elongated hollow body housing 2 which is closed by means of a sliding cover 2a. Inside the chamber C a sutureless fastener member 4 is located.

FIGS. 5A through 5C are directed to the structure inside the elongated hollow body housing 2 excluding the automation system. The biopsy punch device inner structure comprises a biopsy punch cutter 3 assembly and a sutureless fastener member dispenser assembly, wherein the sutureless fastener member dispenser assembly is mechanically coupled to the biopsy punch cutter 3 assembly and located at the same distal end of the elongated hollow body housing 2. However, it is important to understand that in the exemplary embodiment the biopsy punch assembly and sutureless fastener member dispenser work independently from each other.

FIGS. 5A through 5C show biopsy punch cutter 3 assembly comprising a cutter 3 and a cutter shaft 11 (not show in FIG. 5A through 5C) surrounded by the sutureless member dispenser assembly comprising a sutureless path-definer body 8 with flanges 8a, a piston 7, a sutureless fastener member 4, loading shaft 5, a trigger 6, a resilient elastic member 9 and a stopper 10.

FIGS. 6A through 6B provides a cross sectional view of the biopsy punch device showing in more detail the biopsy punch device inner structure in combination with the elongated hollow body housing 2. The biopsy punch cutter 3 assembly comprises a cutter 3, a bearing B and a cutter shaft 11, wherein the cutter shaft 11 comprises a threaded inner surface 111 coupled to the motor shaft 15 which is explained below in more detail. A bearing shaft 12 with a channel or groove 12a surrounds the biopsy punch cutter 3 assembly. The bearing shaft 12 is coupled to the sutureless member dispenser assembly wherein the elastic resilient member 9 is located between the piston 7 distal ends and the stopper 10. The stopper 10 is fixed to the elongated hollow body housing 2. At the front part of the biopsy punch device, close to the cutter 3, a chamber C is created between the path-definer body 8 and the elongated hollow body housing 2. The gap between the path-definer body 8 and the elongated hollow body housing 2 serves as a path for the sutureless fastener member 4.

Figure 7A:
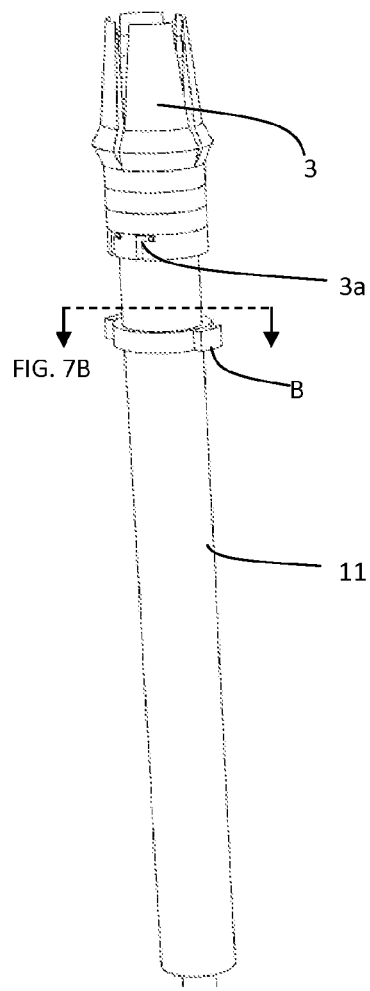
FIGS. 7A through 7C are perspective and cross-sectional views of an exemplary biopsy cutter and biopsy cutter shaft assembly in accordance with the principles of the present example embodiment of the present invention.
Figure 7C:
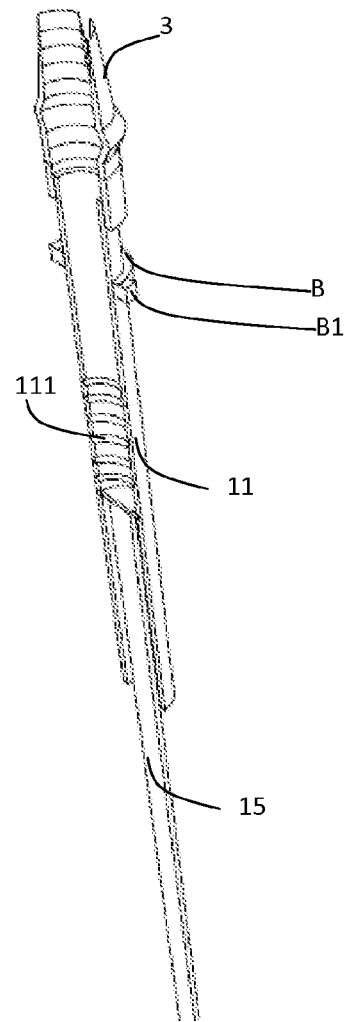
Figure 7B:
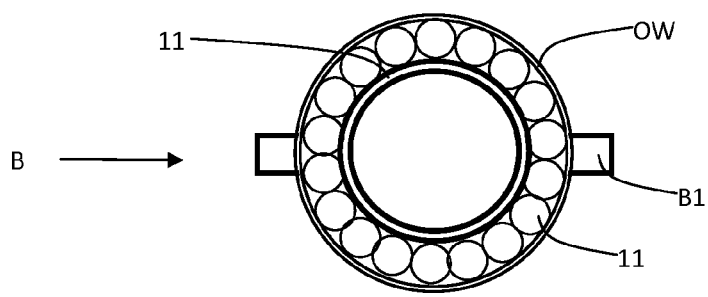

FIGS. 7A through 7C shows more detail of the cutter 3 and cutter shaft 11. FIG. 7A shows the cutter shaft 11 attached to the cutter 3 by attaching means that fixes the cutter 3 in a particular position with respect to the cutter shaft 11. A bearing B is fixed to the cutter shaft 11 at the distal end, wherein the bearing B, such as a ball bearing, surrounds the cutter shaft 11 allowing the rotational movement of the cutter shaft 11 and as result the rotational movement of the cutter 3. The ball bearing B as shown in FIG. 7B comprises an inner wall, wherein the inner wall is the cutter shaft 11, an outer wall OW and several balls located between the cutter shaft 11 and outer wall OW. The bearing B comprises at least two bearing protrusions B1, wherein each bearing protrusion B1 extends away from the bearing B in order to assist with the linear displacement of the cutter shaft 11. Further, the cutter shaft 11, as mentioned above and as shown in FIG. 7C, comprises a threaded inner path 111 forming a helix configuration inner path wherein the motor shaft 15 is mechanically coupled. The motor shaft 15 is intended to through the threaded path 111 exerting a linear displacement of the cutter shaft 11 until it reaches a particular end. While the motor shaft 15 displaces through the threaded path 111 no rotational movement is transmitted to the cutter shaft 11, however when the motor shaft 15 reaches one of the ends and if the rotation of the motor shaft 15 keeps in the same direction the result is the transmission of the rotation from the motor shaft 15 toward the cutter shaft 11. Further, if the rotation of the motor shaft 15 changes directions the result of the change in movement is the linear displacement of the cutter shaft 11 in the direction opposed to the displacement through the treaded path 111. Eventually the motor shaft 15 reaches the opposed end and the rotational movement is transmitted to the cutter shaft 11 in an opposed direction to the rotation achieve when the opposed end is reached.

Figure 9:
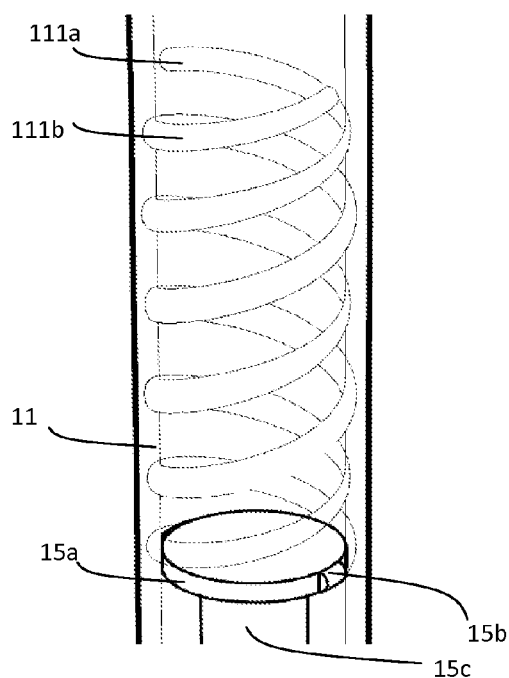
FIG. 9 is an exploded view of an exemplary biopsy cutter shaft inner surface and motor shaft assembly in accordance with the principles of the present example embodiment of the present invention.
Figure 10:
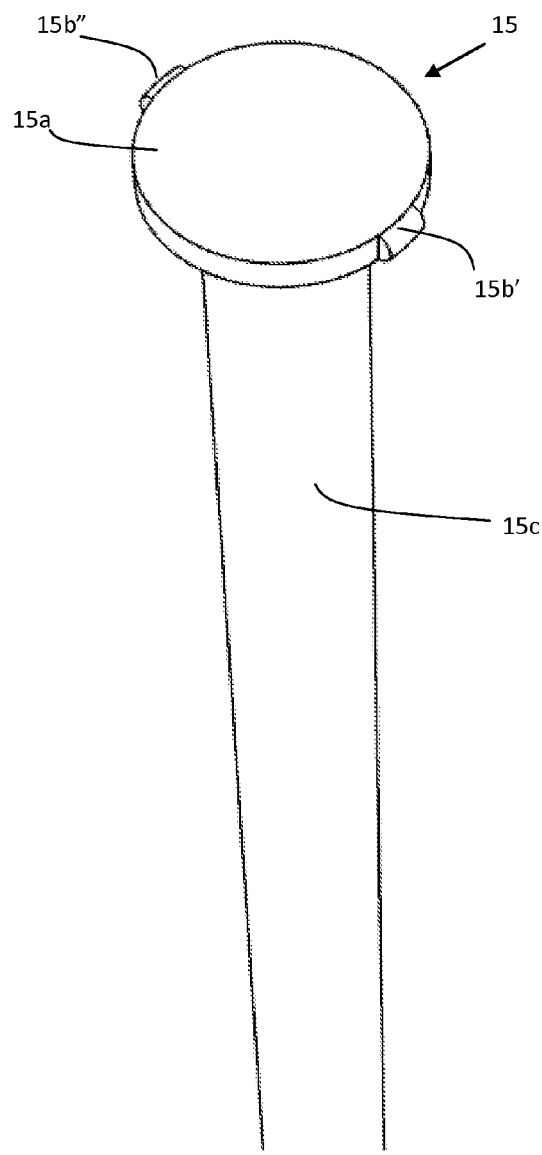
FIG. 10 is an exploded perspective view of an exemplary motor shaft assembly in accordance with the principles of the present example embodiment of the present invention.
Figure 11A:
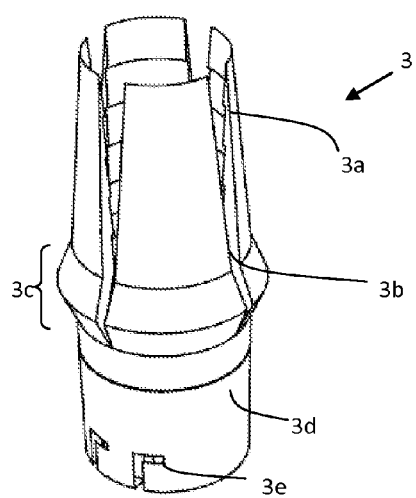
FIGS. 11A through 11B are perspective and exploded views of a first exemplary biopsy cutter fixing means in accordance with the principles of the present example embodiment of the present invention.
Figure 11B:
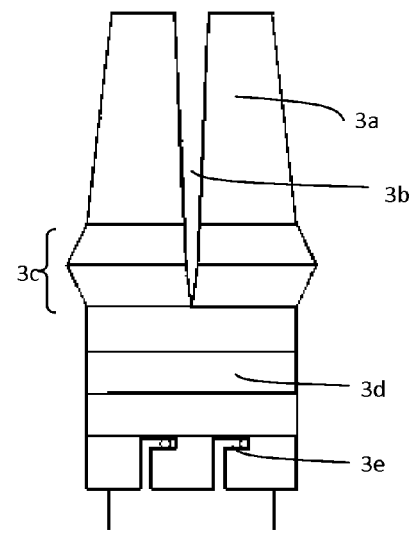
Figure 12A:
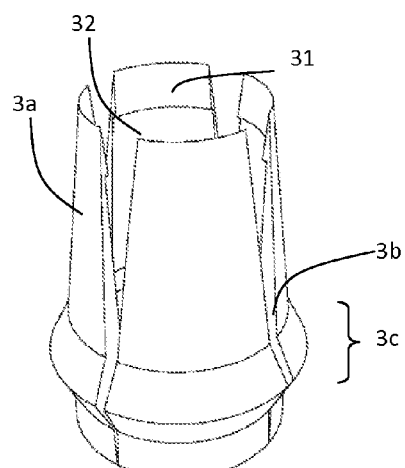
FIGS. 12A through 12E are perspective and exploded views of several exemplary biopsy cutters in accordance with the principles of the present example embodiment of the present invention.
Figure 12B:
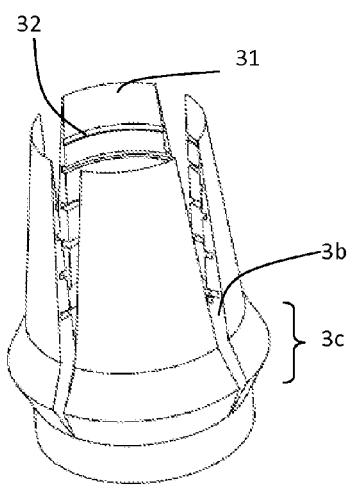
Figure 12C:
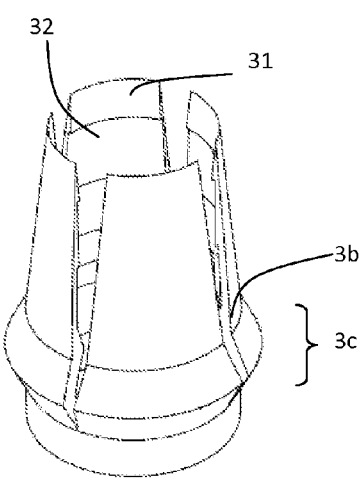
Figure 12D:
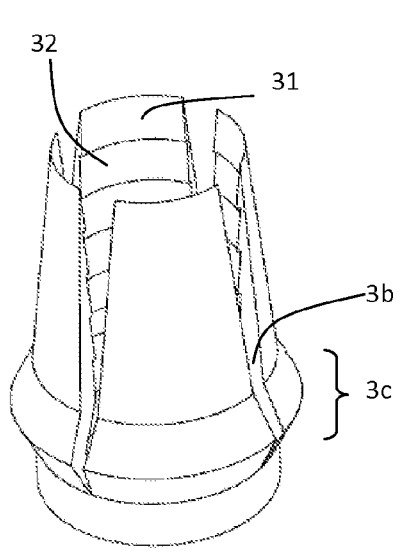
Figure 12E:
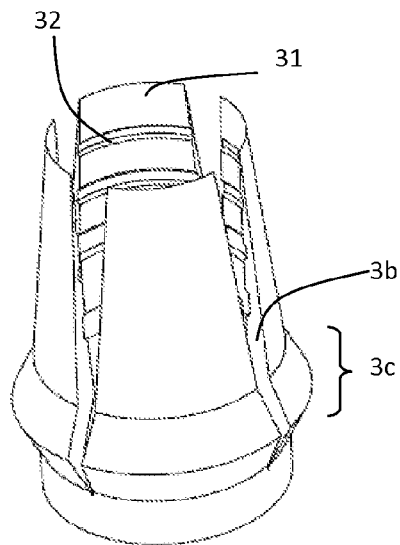
Figure 13:
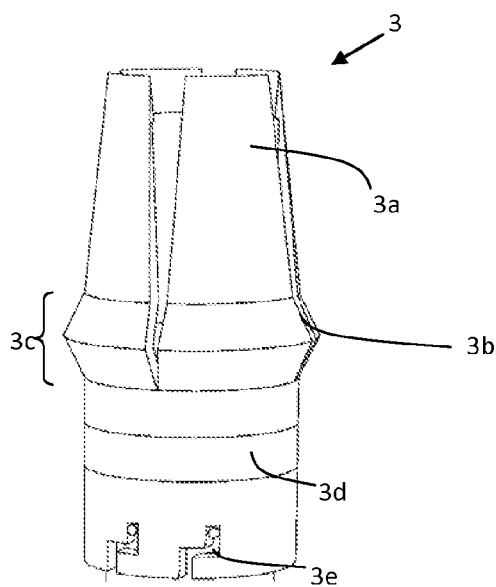
FIG. 13 is a view of a second exemplary biopsy cutter fixing mean in accordance with the principles of the present example embodiment of the present invention.
Figure 14:
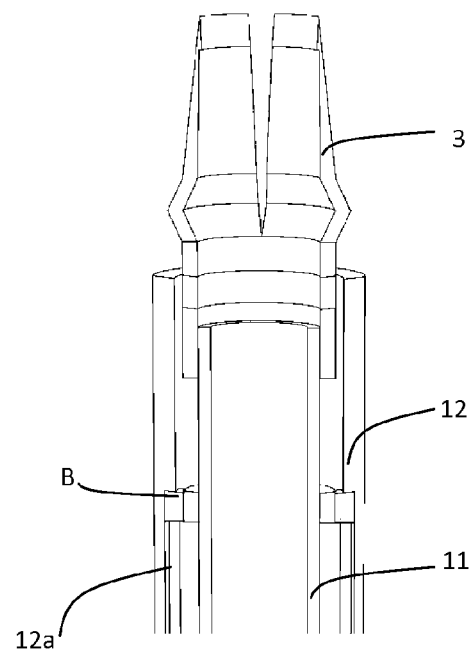
FIG. 14 is a cross-sectional view of a biopsy cutter coupled to the cutter shaft in accordance with the principles of the present example embodiment of the present invention.

FIG. 8A through FIG. 8B show in more details the shaft cutter 11, wherein the shaft cutter 11 comprises several projections 11b at the distal end serving as the attaching means, as previously mentioned. The threaded path 111 comprises a first helical groove 111a and a second helical groove 111b. The use of two helical grooves 111a, 111b assists with the stability of the cutter shaft 11 displacement and rotation. FIG. 9 clearly shows the threaded inner path 111 with the surface first spiral groove 111a and a second helical groove 111b wherein the motor shaft 15 travels. The rotational movement of the motor shaft 15 results in a linear displacement of the cutter shaft 11 as long the motor shaft 15 does not reaches any of the two ends of the threaded inner path 111. In order to provide the rotational movement of the motor shaft 15 inside the cutter shaft 11 and through the threaded inner path 111 the motor shaft 15 is provided with at least a first extension 15b' and a second extension 15b", both located at the distal end the motor shaft 15, as showed in FIG. 10. The first extension 15b' and a second extension 15b" travel along the first spiral groove 111a and the second spiral groove 111b respectively. Further the motor shaft 15 comprises a flat surface 15a from where the first extension 15b' and a second extension 15b" extends.

FIG. 11A through 14 are directed to the cutter 3. The cutter 3 comprises at a plurality of blades 3a made of an inexpensive and durable metal and/or plastic materials such as stainless steel blade, a middle cutter body 3c, tapered gap 3b, a cutter base 3d arranged and fixing means 3e. The plurality of blades 3a is arranged in a substantially circular contour, wherein each blade 3a is separated by the tapered gap 3b. The tapered gap 3b extends from the blade 3a through the middle cutter body 3c until reaching the cutter base 3d as show in FIG. 11B.

The inner surface of the blades 3a comprises at least one rib 31 which is formed by reducing the inner surface. The reduction of the inner surface is achieved by blades grooves 32. The ribs 31 assists with the grasping and removing of the tissue sample, therefore the configuration of the ribs 31 depends on the particular action to be performed by the cutter 3. For example, it is preferred in to have a cutter 3 with just one rib 31 in order to obtain a tissue example, as show in FIG. 13 and FIG. 14, because multiple ribs may causes damages to the tissue sample instead of assisting with the grasping of the sample.

Further the middle cutter body 3c is shaped to comprise an articulate configuration. The articulate configuration connects the blades 3a and the cutter base 3d. The articulate configuration serves to promote a distal compression at the tips of the blades 3a when the articulation 3d is compressed during the retraction of the cutter 3 inside the hollow body of the cutter shaft 11.

The tapered gap 3b allows the compression of the cutter 3 without the deformation of neither the blades 3a nor the cutter base 3d while the compressing force is exerted at the middle cutter body 3c. While applying compressing force to the middle body 3c the tapered tap or space between the blades 3 is reduced and simultaneously the middle body 3c articulated section is flattened. The space reduction results in a reduction of diameter at the distal end of the blade 3 and serves as a grasping action which is assisted, as mentioned before, by ribs 31 located at the inner surface of the blade 3a.

The compressive action or force applied to the middle body 3c is achieved during the rotation of the motor shaft 15 that results in the linear displacement of the cutter shaft 3, more particular in the linear displacement of the cutter 3 toward the inner surface of the bearing sleeve 12.

FIG. 15A through 16 are directed to the bearing sleeve 12. The bearing sleeve 12 comprises a cylindrical elongated hollow body 12 with a set of channels 12a located at the inner surface of the elongated hollow body 12. The cutter shaft 11 is mechanically coupled to the bearing sleeve 12 by means of the bearing protrusions B1. The bearing sleeve 12 limits the linear movement of the cutter shaft 11 while covers part of the cutter base 3d and cutter shaft 11. The channels serves as guides for the bearing protrusion B1 during the linear displacement of the cutter shaft 11.

The bearing sleeve 12 further comprises a compressing surface 12b. In the instant case the compressing surface 12b is a flat surface, however it can be a tapered zone toward the inner surface of the bearing sleeve 12 in order to provide smooth contact with the middle body 3c. During the linear displacement of the cutter shaft 11 toward the motor M the cutter 3 retracts as result of the mechanical connection with cutter shaft 11. The articulation of the middle body 3c comprises an increment in diameter, wherein the middle body 3c diameter fluctuates from a diameter smaller than the bearing sleeve 12 to a maximum diameter bigger than the bearing sleeve 12. During the linear displacement of the cutter shaft 11, due to rotational motion of the motor shaft 15, the middle body 3c, more particularly the area of the middle body 3c wherein the diameter is bigger than the bearing sleeve 12, is compressed by the compressing surface 12b. The compressing action is performed from the middle body 3c closer to the cutter base 3d toward the blades 3a. As explained above, the deformation of the blade 3a is avoided by the tapered gap 3b.

Figure 17A:
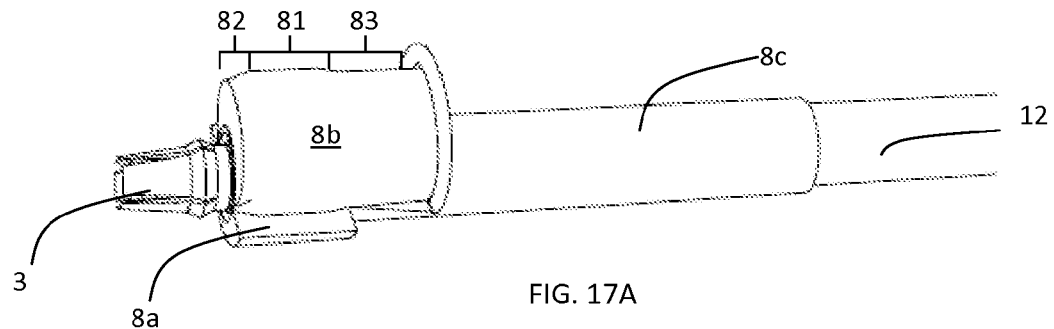
FIGS. 17A through 17B are several views of an exemplary biopsy closure member path-definer element in accordance with the principles of the present example embodiment of the present invention.
Figure 17B:
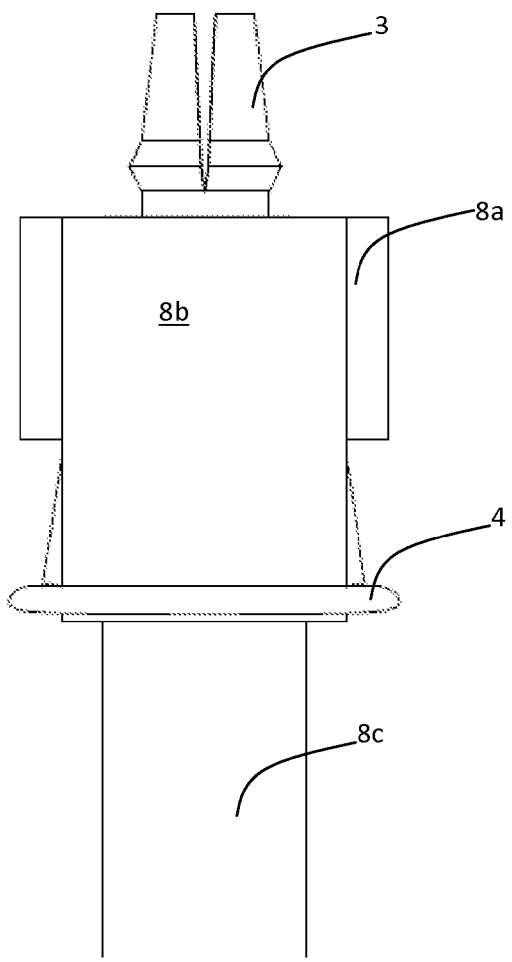

After the cutter 3 incises the patient and removes the tissue example from the patient an open wound is left in front of the biopsy punch device 1. The biopsy device 1 is equipped with a sutureless system comprising a sutureless member dispenser assembly, as mentioned before. FIG. 17 through 21 discloses in detail the sutureless system, more particularly sutureless fastener member 4 dispenser assembly comprising a sutureless path-definer body 8 with flanges 8a, a piston 7, a sutureless fastener member 4, loading shaft 5, a trigger 6, a resilient elastic member 9 and a stopper 10, as mentioned before. FIGS. 17A and 17B are directed to the sutureless path-definer body 8. The sutureless path-definer body 8 comprises a sutureless path-definer main body 8b, flanges 8a and an sutureless path-definer elongated body 8c. The sutureless path-definer body 8 is fixed to the housing 2 therefore avoiding rotation of the structure with respect to the housing 2. The sutureless path-definer main body 8b and flanges 8a serves as a path for the sutureless fastener members 4, wherein said sutureless fastener member 4 is positioned around the sutureless path-definer main body 8b.

The contour of the sutureless path-definer body 8b comprises a proximal end 82, central section 81 and a distal end 83. The central section 81 comprises an increment in dimensions, more particularly in the circumferential dimensions, wherein the diameter achieves an increment in diameter when compared with the proximal end 82 and a distal end 83. The proximal end 82 is configured to have a tapered contour which results in a smooth surface with a decreased diameter assisting with the traveling of the sutureless fastener member 4 through the path-definer body 8b until reaching the patient's skin. At the distal end 83 the contour is configured to assists with the fixing of the fastener member 4 during the loading procedure before it is pushed by the piston 7. The configuration and arrangement of the proximal end 82, central section 81 and a distal end 83 makes the impact and insertion of the sutureless fastener member 4 in the patient's skin more comfortable since the change in dimension reduce the impact force of the sutureless fastener member 4 and simultaneously assists with the insertion of the fastener member while traveling through the proximal end 82. In the instant case the sutureless path-definer body 8 surrounds the biopsy punch cutter assembly.

Figure 18A:
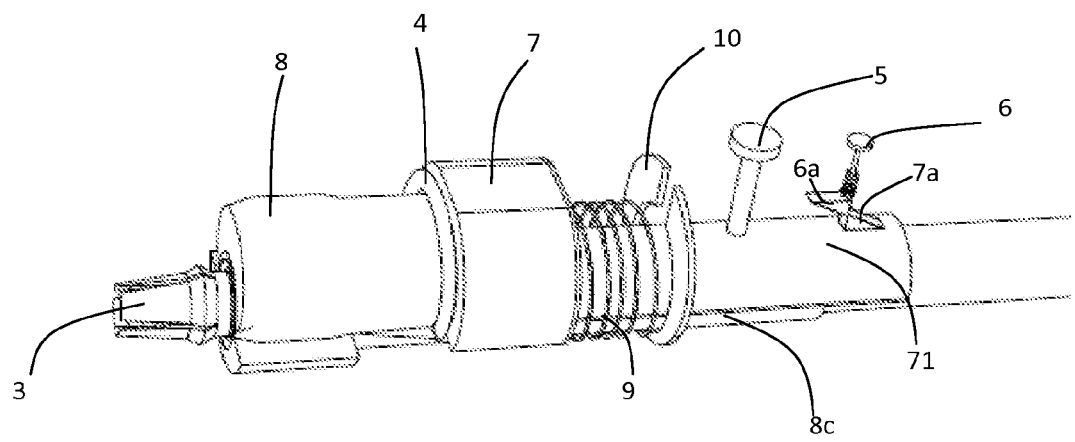
FIGS. 18A through 18C are several views of an exemplary sutureless mechanism assembly in accordance with the principles of the present example embodiment of the present invention.
Figure 18B:
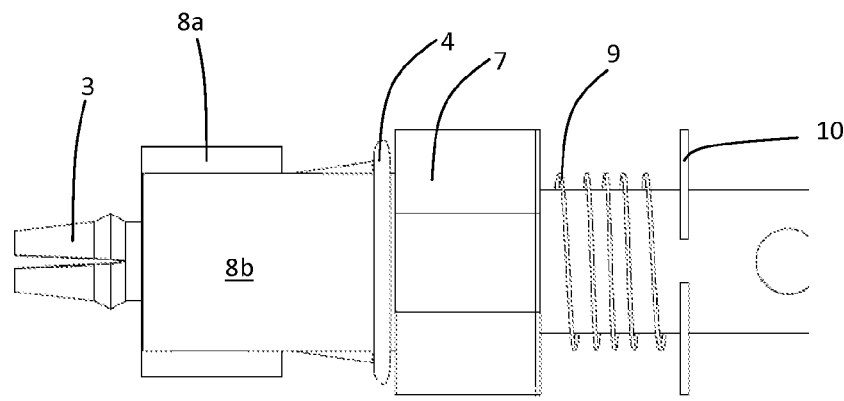
Figure 18C:
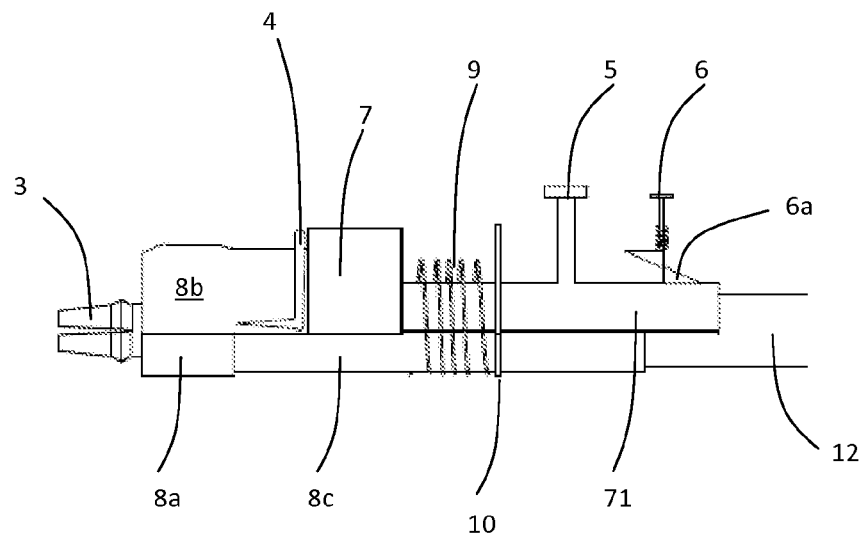

FIGS. 18A through 18C are directed to the assembling between the sutureless path-definer body 8 and the piston 7. The piston comprises a piston head 7a and a piston loading body 71, wherein said piston loading body 71 comprises the loading shaft and a trigger stopper 6a. The piston loading body 71 surrounds the sutureless path-definer elongated body 8c and the piston head 7a further surrounds a portion of the sutureless path-definer body 8b and the sutureless path-definer elongated body 8c.

A resilient elastic member 9, such as a spring, is positioned between the stopper 10 and the piston head 7a, as previously mentioned. During the sutureless procedure the spring 9 is in a loading position wherein the loading position is defined as a position wherein said spring 9 is compress between the stopper 10 and the piston head 7a. In order to compress the spring 9 the piston 7 is pushed back by means of the loading shaft 5. After reaching a pre-determinate compression force at the spring 9 the position is locked by means of a trigger 6 and trigger stopper 6a. The sutureless fastener member 4 is then located or positioned in front of the piston head when the loading position is achieved. The sutureless fastener member 4 is designed to travel through the sutureless path-definer body 8b when the trigger 6 is released and as result the decompression of the spring 9 provides enough force pushing sutureless fastener member 4 towards the open wound site.

Figure 19A:
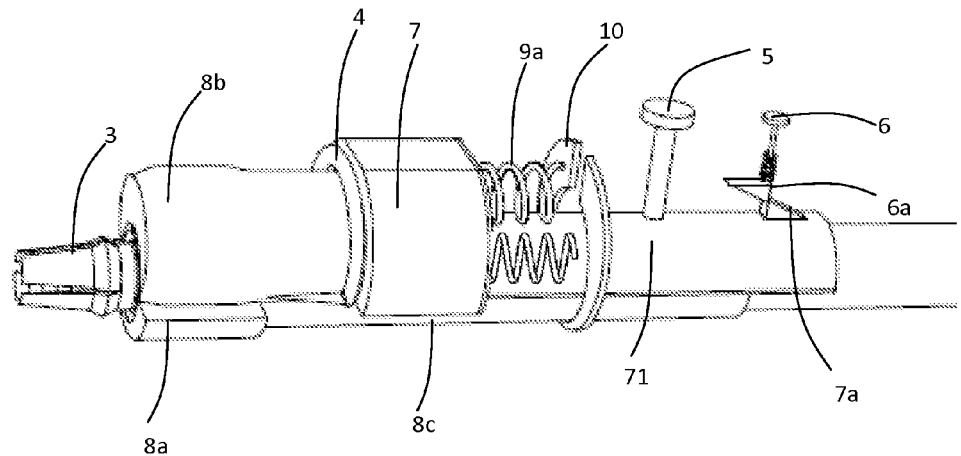
FIGS. 19A through 19B are several views of an exemplary sutureless mechanism assembly with alternative elastic member configurations in accordance with the principles of the present example embodiment of the present invention.
Figure 19B:
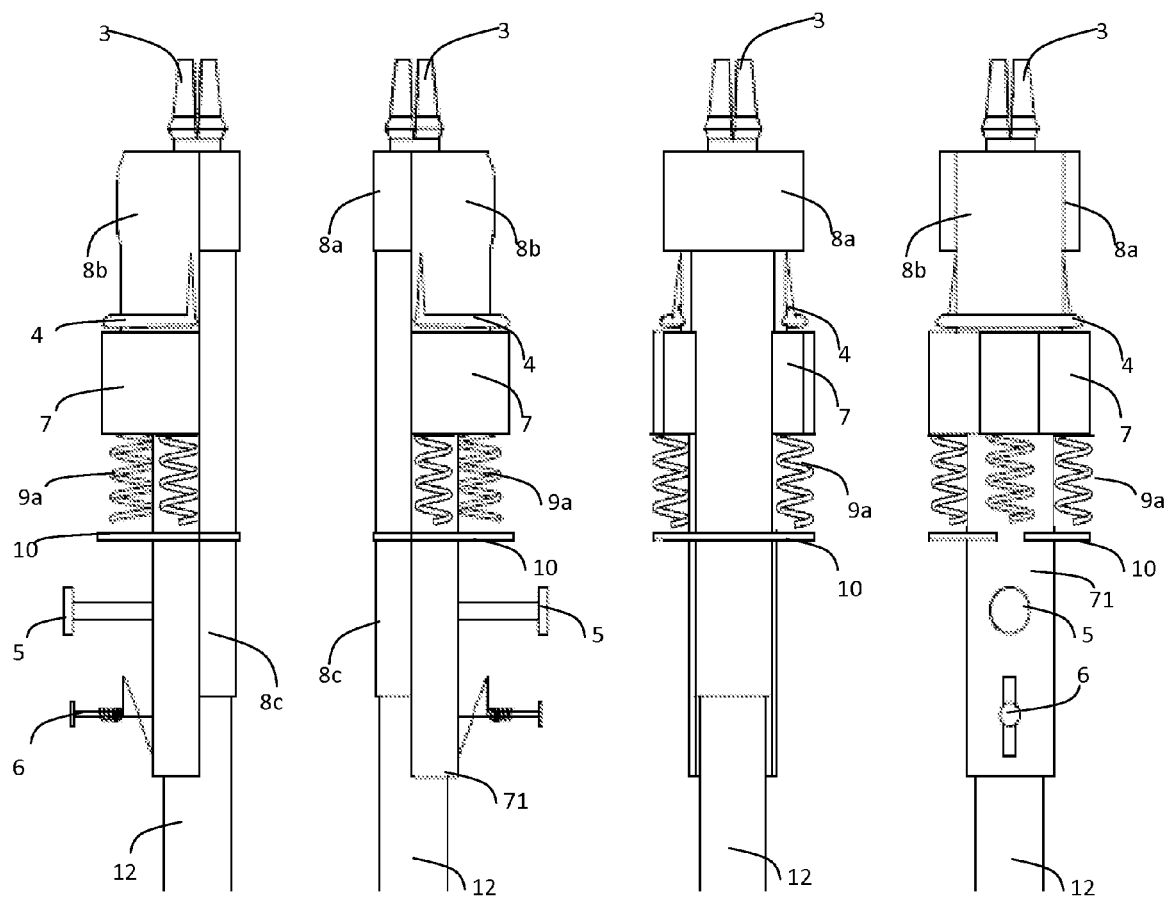

Several resilient elastic members or different resilient elastic member configuration or means to achieve the pushing action of the piston 7 can be used. FIG. 19A through FIG. 19B discloses the use of a plurality of spiral springs 9a to performed the pushing action for the sutureless member 4.

Figure 20:
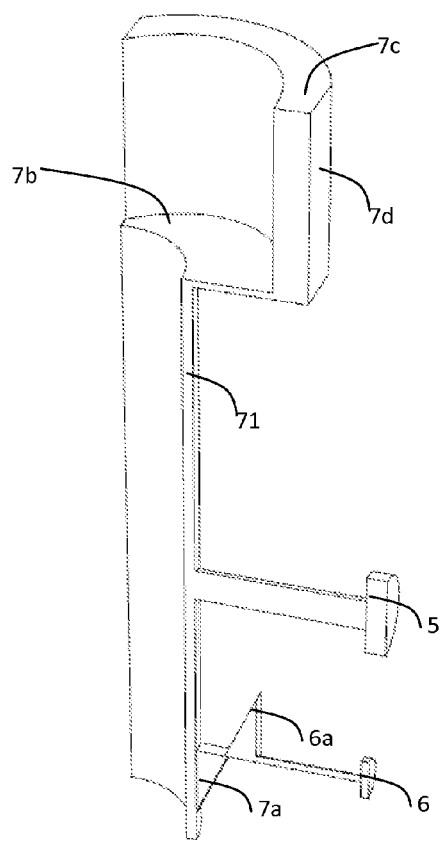
FIG. 20 is a cross-sectional view of an exemplary sutureless mechanism actuator in accordance with the principles of the present example embodiment of the present invention.
Figure 21:
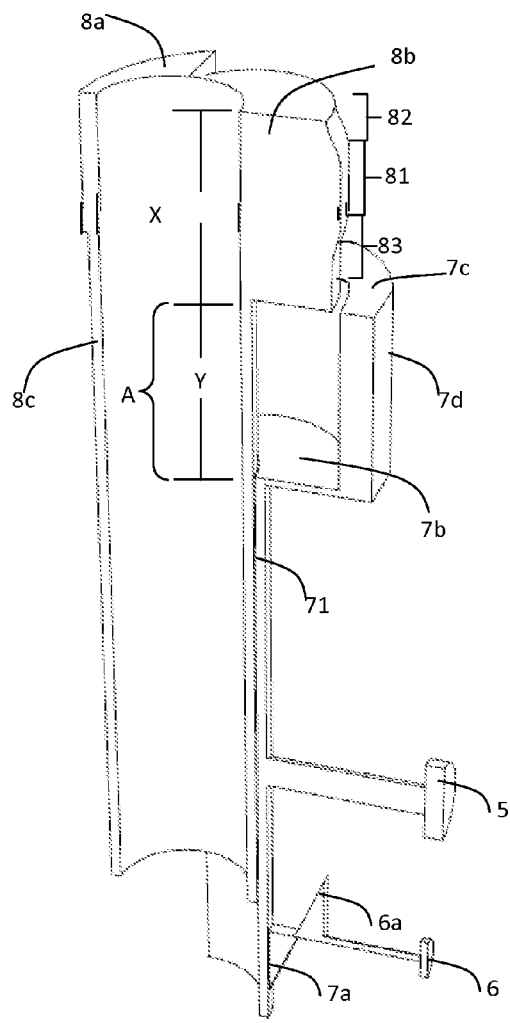
FIG. 21 is a cross-sectional view of an exemplary sutureless mechanism actuator assembly in accordance with the principles of the present example embodiment of the present invention.

FIG. 20 show in more detail the piston 7, wherein the piston comprises piston head 7a and a piston loading body 71, wherein said piston loading body 71 comprises the loading shaft 5 and a trigger stopper 6a, as mentioned previously. Further the piston comprises a piston chamber A with a piston chamber bottom surface 7b and a piston contact surface 7c. The piston contact surface 7c is designed to be in close contact with the sutureless fastener member 4 during the pushing action. The piston chamber A comprises a space with dimensions big enough to receive the sutureless path-definer 8b main body. FIG. 21 provides a cross sectional section of the assembly between the piston 7 and the sutureless path-definer body 8. The chamber A length is desired to be equal to or bigger than the sutureless main body 8b length X in such way that the sutureless fastener member 4 travels the sutureless main body 8b with the piston contact surface 7c constantly pushing the sutureless fastener member 4. However it is important to understand that the current dimension may vary depending of factor such as the elastic properties of the elastic member 9 which result in the decompression force, and the friction of the sutureless fastener member 4 with the sutureless main body 8b. The contour of sutureless path-definer body 8b, as mentioned above, assists with the traveling of the sutureless fastener member 4.

Figure 22:
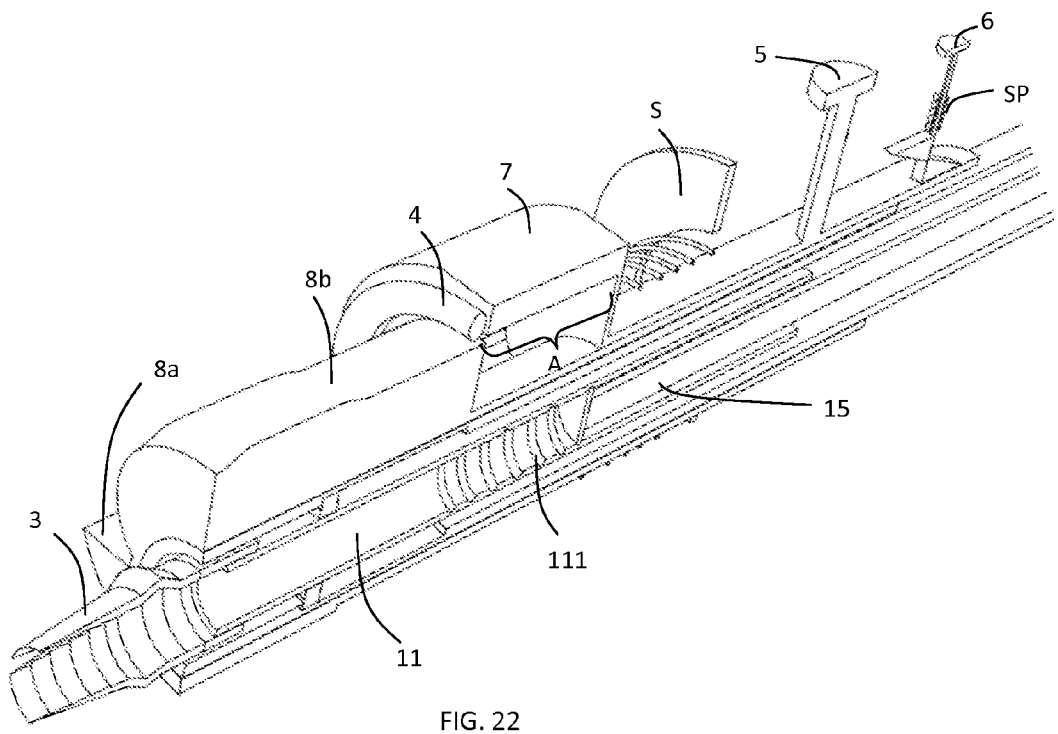
FIG. 22 is a cross-sectional view of an exemplary sutureless mechanism actuator assembly in accordance with the principles of the present example embodiment of the present invention.

FIG. 22 is directed to a cross sectional view of the sutureless member dispenser assembly surrounding the biopsy punch cutter 3 assembly, wherein the contact between the sutureless fastener member 4 is clearly show to be in contact with the piston contact surface 7c. The device is loaded when the sutureless fastener member 4 is positioned in front of the piston contact surface 7c while the resilient member 9 is compress and in position to be release by means of the trigger 6. The chamber length A, as explained above, limits the range of motion for the piston 7.

Figure 23:
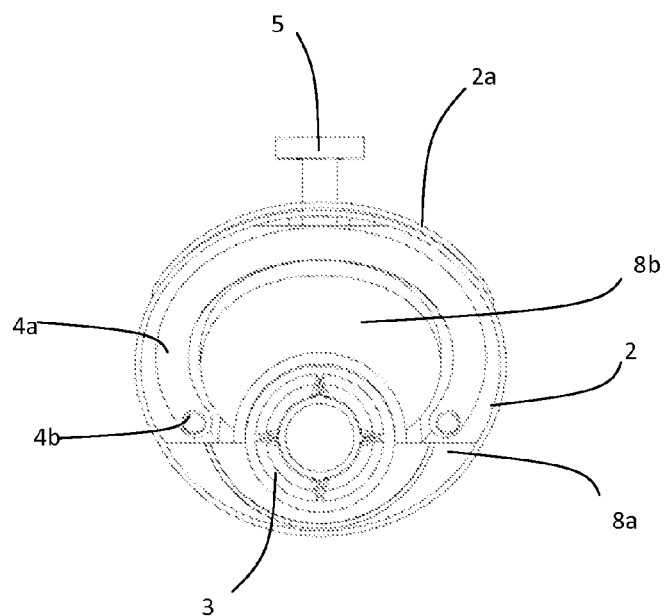
FIG. 23 is a front view of an biopsy punch device in accordance with the principles of the present invention.

FIG. 23 is a front view of the exemplary biopsy punch device in accordance with the principles of the present invention wherein the front chamber C is created at the front part of the elongated hollow body housing 2 wherein the sutureless fastener member 4 travels path-definer during the decompression action.

Figure 24A:
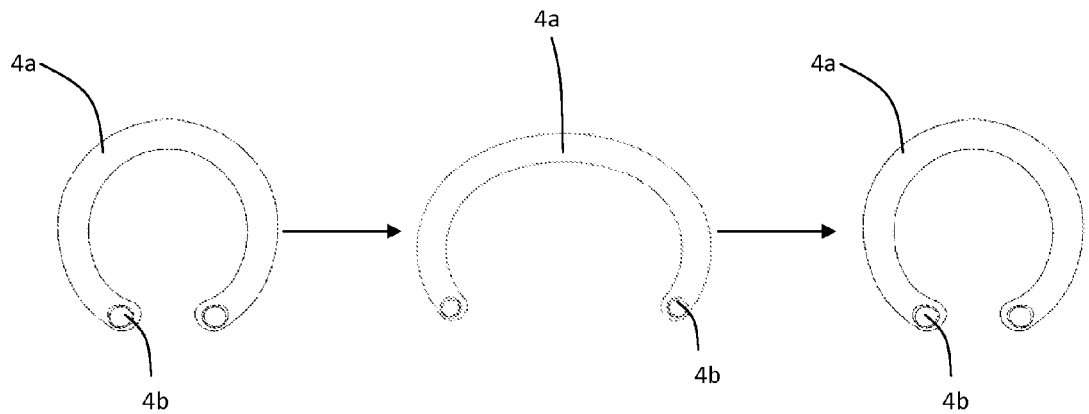
FIGS. 24A through 24C are several views of an exemplary biopsy closure or sutureless fastener member in accordance with the principles of the present example embodiment of the present invention.
Figure 24B:
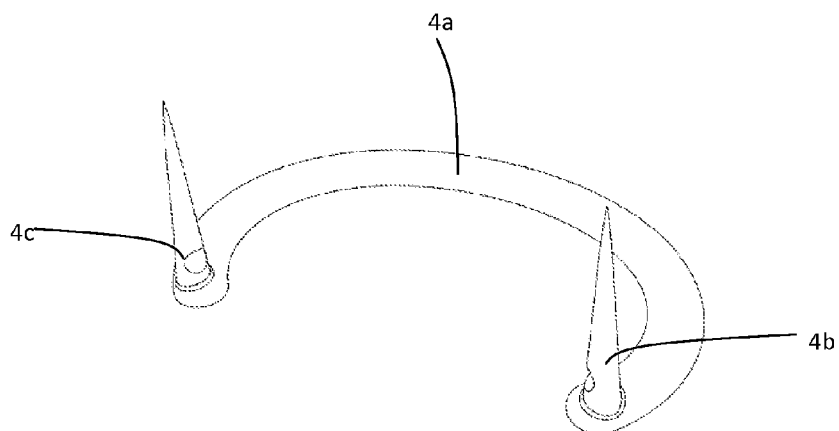
Figure 24C:
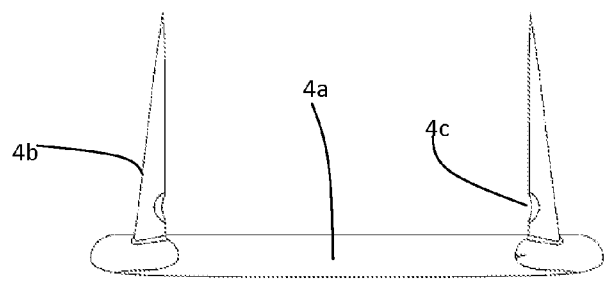

FIG. 24A through 24C discloses the sutureless fastener member 4. The sutureless fastener member 4 or biopsy closure fastener member comprises two prongs 4b connected by a fastener body 4a serving as a bridge between the prongs. The fastener body 4a has resilient properties, wherein the two-pronged 4b fastener may expand to a distance bigger than the diameter of the wound created by the cylindrical cutter, as shown in FIG. 24A. The fastener body material is selected from a group or resilient plastic material, resilient ceramic plastic, resilient metal material or any combination. The resilient material selected has to be a no-toxic resilient material.

The two-pronged fasteners 4b are intended to be inserted at opposite sides of the wound site into the patient's skin. The sutureless fastener member 4 is stretched in order to be inserted into the patient's skin at opposite sides of the wound site. The stretching action is assisted by the path-definer body 8b which keeps the two-pronged fasteners 4b separated enough to have a distance bigger than the diameter of the wound created by the cylindrical cutter 3. After the sutureless fastener member 4 is inserted into the patient's skin the resilient properties of the sutureless fastener member 4 acts on the wound site. Since no rigid body is retraining the fastener member 4 stretched the fastener member 4 returns to its original form consequently making the opposite sides of the wound to come together. The resilient properties of the sutureless member 4 close the wound without the need of additional instruments.

The two-pronged 4b comprises a recess 4e, wherein said recess 4c assists with the fastener member 4 action of pulling together the opposite sides of the wound site. Therefore the sutureless biopsy closure dispenser releases the biopsy closure member 4 at the wound site which renders the biopsy wound site close by approximating the opposing edges of the wound. In addiction the fastener member 4 may be coated with a medicinal drug or substance, such as an antibacterial.

Figure 25:
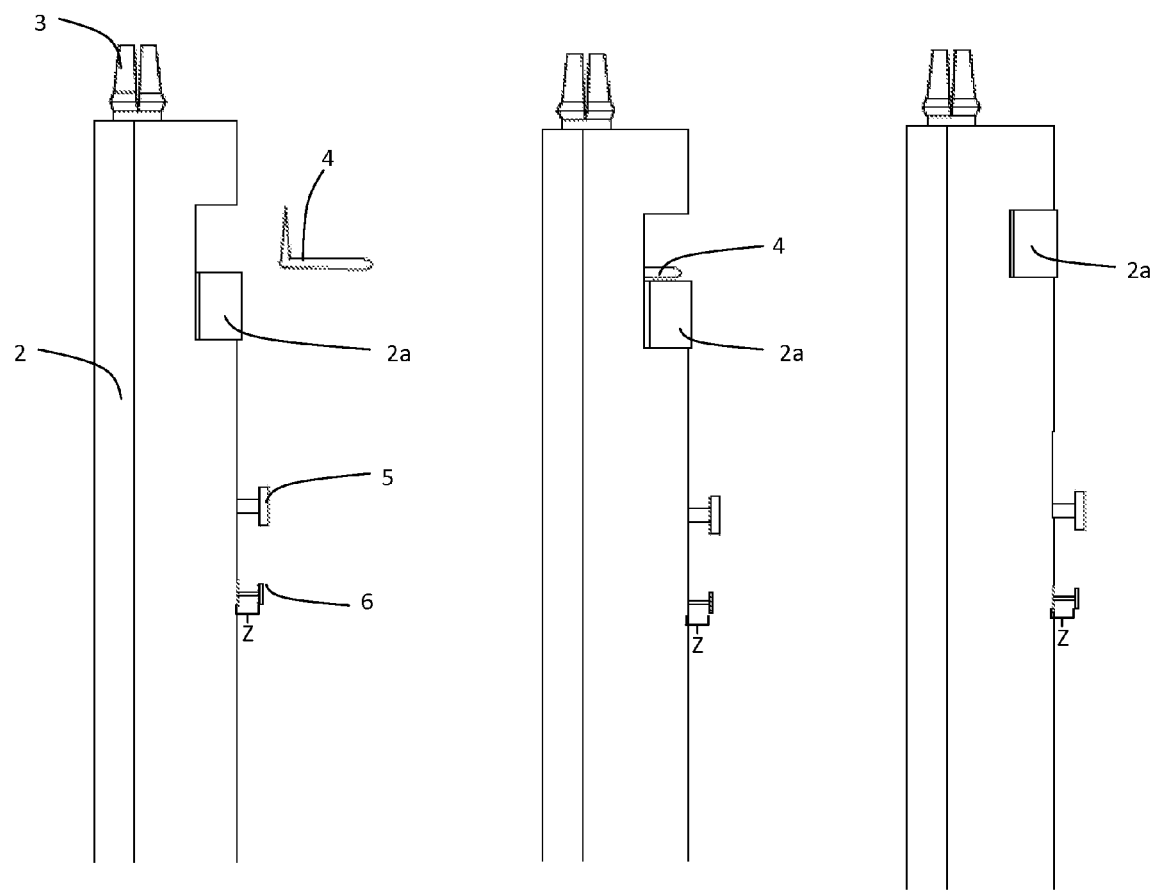
FIG. 25 shows the loading process for the biopsy closure member in the biopsy punch device in accordance with the principles of the present example embodiment of the present invention.

FIG. 25 is directed to the loading of the sutureless fastener member 4, wherein the sutureless fastener member 4 is positioned inside chamber C, as explained before. After the sutureless fastener member 4 is expanded and located around the path-definer main body 8b, more particularly main body distal end 83. Further, the opening to access chamber C is closed by means of a cover 2a. At this instant the biopsy device 1 is loaded and ready to remove the tissue sample as explained before. While performing the biopsy the motor is controlled to rotate in a particular direction providing the rotation at the cutter 3 without linear displacement, as explained above. After the incision is performed the motor M is controlled to rotate in the opposite direction in such way that the cutter 3 is retracted and the tissue is removed from the patient.

Figure 26:
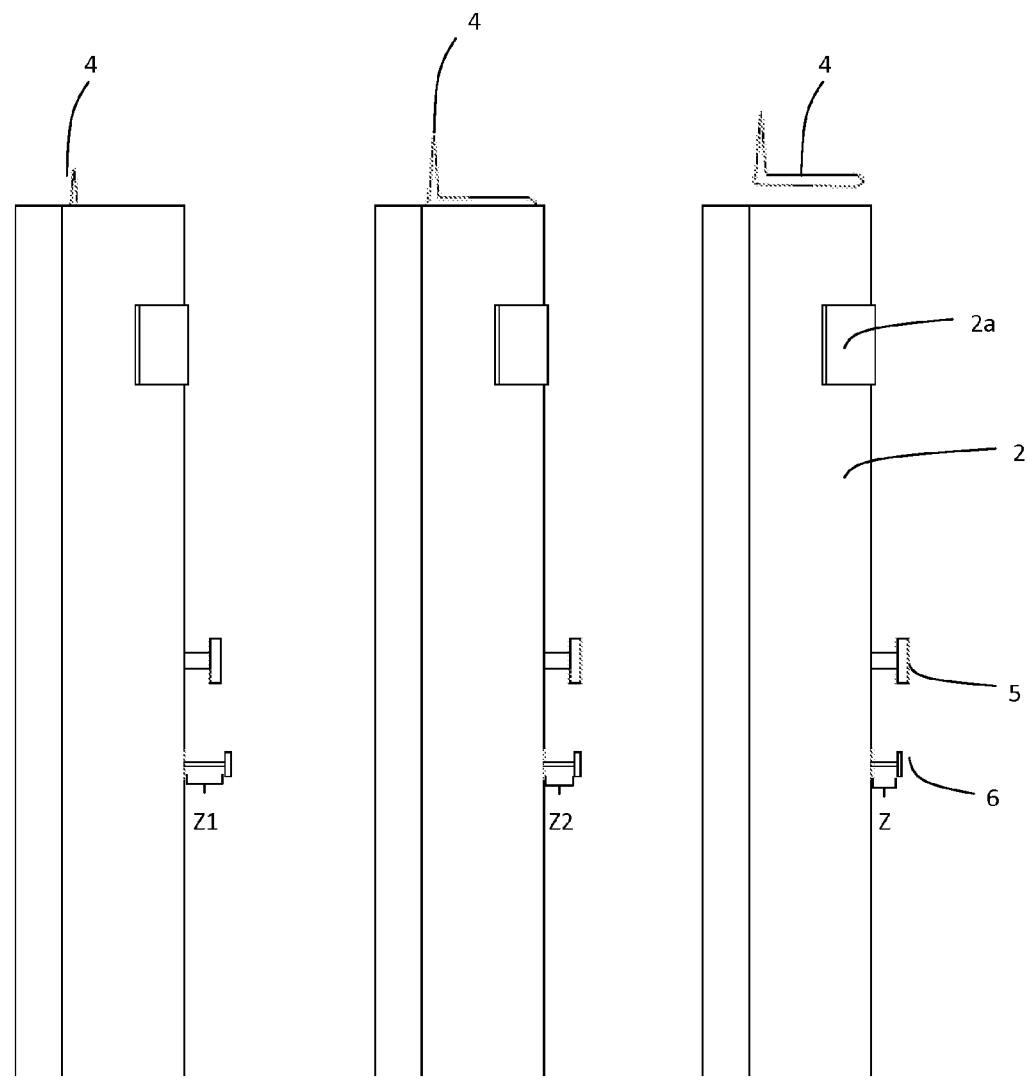
FIG. 26 shows the biopsy closure member releasing process in accordance with the principles of the present example embodiment of the present invention.

FIG. 26 is directed to the process after the cutter 3 is retracted. First the trigger 6 is activated Z1 in such way that the piston 7 is released and the sutureless fastener member 4 is pushed toward the patient's skin. Second the fastener member 4 is inserted into the patient's skin, more particularly the two prong 4b parts at opposite side of the wound site as result of the pushing action of the piston 7 as explained above. Further the biopsy devise 1 is remove and the sutureless resilient member 4 compresses the opposite side wound wherein the prongs 4b are inserted pulling together said opposite sides of the wound site. The wound can be covered with a substance that kills bacteria or slows their growth. Further a bandage may be used to support or hold the fastener member 4 in position.

While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

The invention claimed is:
1. A biopsy punch device comprising:
(a) a housing comprising a proximal end and a distal end,
(b) a biopsy punch cutter assembly surrounded by the housing, wherein said cutter assembly includes an elongated hollow cutter shaft comprising:
(i) a cutter shaft distal end, and,
(ii) a cutter comprising an articulated section, wherein said cutter extends distally from said distal end of said housing, wherein said cutter is coupled to the cutter shaft distal end and wherein said cutter shaft is con- figured to provide linear and rotational displacements of the cutter with respect to the distal end of said housing;

(c) a bearing shaft located within said housing, wherein said bearing shaft surrounds the biopsy punch cutter assembly, wherein said cutter extends distally from a distal end of said bearing shaft, wherein said articulated section comprises a diameter that is larger than an inner diameter of said bearing shaft, and wherein said bearing shaft and articulated section are configured such that the bearing shaft flattens said articulated section and thereby reduce said diameter of said articulated section during said linear displacement of said cutter;

(d) a suture-less fastener member for closing a wound in tissue, wherein said suture-less fastener member surrounds said biopsy punch cutter assembly;

(e) a suture-less fastener member dispenser assembly for dispensing the suture-less fastener member, wherein said dispenser assembly comprises a loading mechanism and a trigger; and (f) an actuator assembly comprising an actuator mechanism for providing a linear and rotational displacement to the cutter shaft.

2. A biopsy punch device as in claim 1, wherein said actuator assembly comprises an automatic system comprising a motor, motor shaft and a control system, wherein said motor shaft serves as the actuator mechanism.

3. A biopsy punch device as in claim 2, wherein said automatic system is located at the proximal end of an elongated hollow body and; wherein said motor shaft is mechanically coupled to the biopsy punch cutter assembly.

4. A biopsy punch device as in claim 2, wherein the biopsy punch cutter assembly comprises:
the hollow cutter shaft comprising a cutter shaft proximal end and threaded inner surface;
wherein said threaded inner surface extends from cutter shaft distal end, a cutter shaft proximal end, wherein the cutter shaft proximal end is coupled to the motor shaft; and
a bearing, wherein said bearing surrounds said hollow cutter shaft.

5. A biopsy punch device as in claim 1, wherein said suture-less fastener member comprises a fastener body a first prong and second prong, wherein said fastener body comprises a fastener distal end and a fastener proximal end, wherein the first prong extend perpendicular to the fastener body and is located at the fastener distal end and wherein the second prong extend perpendicular to the fastener body and is located at the fastener proximal end.

6. A biopsy punch device as in claim 5, wherein the fastener body in made from material selected from resilient plastic material, resilient ceramic material or resilient metal material.

7. A biopsy punch device as in claim 1, wherein said suture-less fastener member dispenser assembly comprises:
a suture-less path-definer body comprising a suture-less path-definer main body, flanges and a suture-less path-definer elongated body, wherein a chamber is created between suture-less path-definer main body, flanges and said housing,
a piston and a stopper.

8. A biopsy punch device as in claim 7, wherein said housing comprises an opening for accessing the chamber, wherein said suture-less fastener member is inserted.

9. A biopsy punch device as in claim 7, wherein said piston comprises a piston head and a piston loading body, wherein said piston loading body comprises a trigger stopper, wherein said loading shaft is coupled to the piston.

10. A biopsy punch device as in claim 7, wherein said stopper is coupled to the housing, wherein an elastic material is located between the piston head and said stopper.

11. A biopsy punch device as in claim 1 wherein the bearing shaft surrounding the biopsy punch cutter assembly comprises grooves, wherein said grooves serves to provide a limited linear displacement for the bearing shaft.

12. A biopsy punch device as in claim 1 wherein the cutter comprises at least a blade, a tapered gap, a middle cutter body and a cutter base, wherein the middle cutter body comprises said articulated section.

* * * * *